United States Patent [19]

Thompson et al.

[11] Patent Number: 5,489,275
[45] Date of Patent: Feb. 6, 1996

[54] IDENTIFICATION RING FOR CATHETER

[75] Inventors: Russell B. Thompson, Los Altos; David McGee, Palo Alto, both of Calif.

[73] Assignee: EP Technologies, Inc., Sunnyvale, Calif.

[21] Appl. No.: 338,336

[22] Filed: Nov. 14, 1994

[51] Int. Cl.⁶ .................................................. A61M 5/00
[52] U.S. Cl. ........................ 604/264; 604/95; 604/111; 604/282
[58] Field of Search .......................... 604/95, 280, 281, 604/282, 159, 264, 111, 189, 100, 283; 128/772

[56] References Cited

U.S. PATENT DOCUMENTS

| | | | |
|---|---|---|---|
| 5,199,950 | 4/1993 | Schmitt et al. | 604/282 X |
| 5,219,332 | 6/1993 | Nelson et al. | 604/95 |
| 5,267,573 | 12/1993 | Evans et al. | 604/95 X |
| 5,273,535 | 12/1993 | Edwards et al. | 604/95 |

*Primary Examiner*—John D. Yasko
*Attorney, Agent, or Firm*—Ryan, Maki & Hohenfeldt

[57] ABSTRACT

A catheter assembly which has a distal end adapted for insertion into a living body and a proximal end adapted to remain external to said body or a cable for use in such an assembly includes a cylindrical surface on which are inscribed a plurality of markings. Each of the markings indicates one of the specific locations within the living body at which the distal end may be placed during insertion. The markings are positioned at spaced intervals around the circumference of the cylindrical surface. A sleeve is rotatably and/or axially movable around the cylindrical surface, the sleeve being provided with at least one window adapted to be moved into alignment with a selected one of the markings.

13 Claims, 4 Drawing Sheets

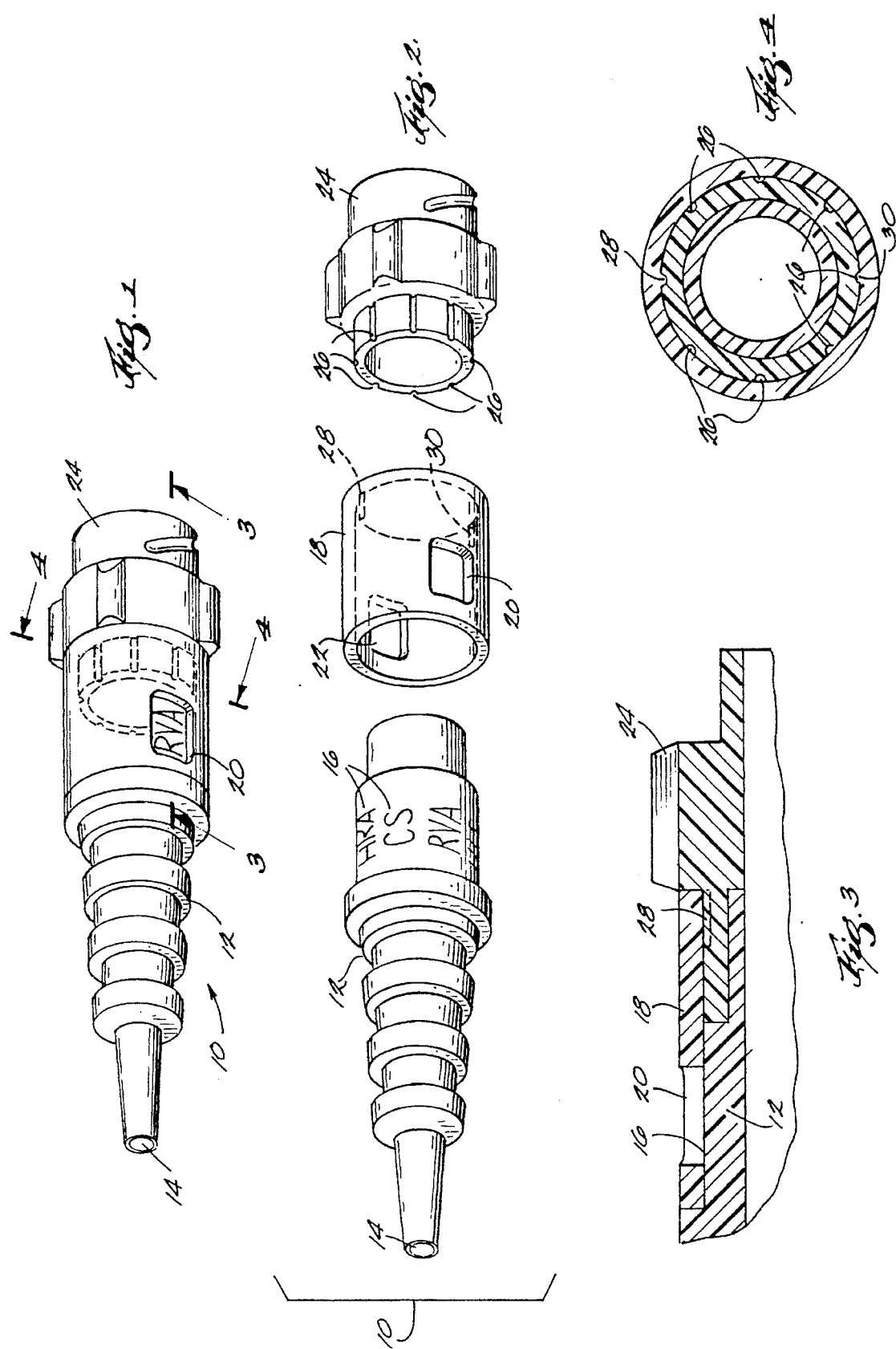

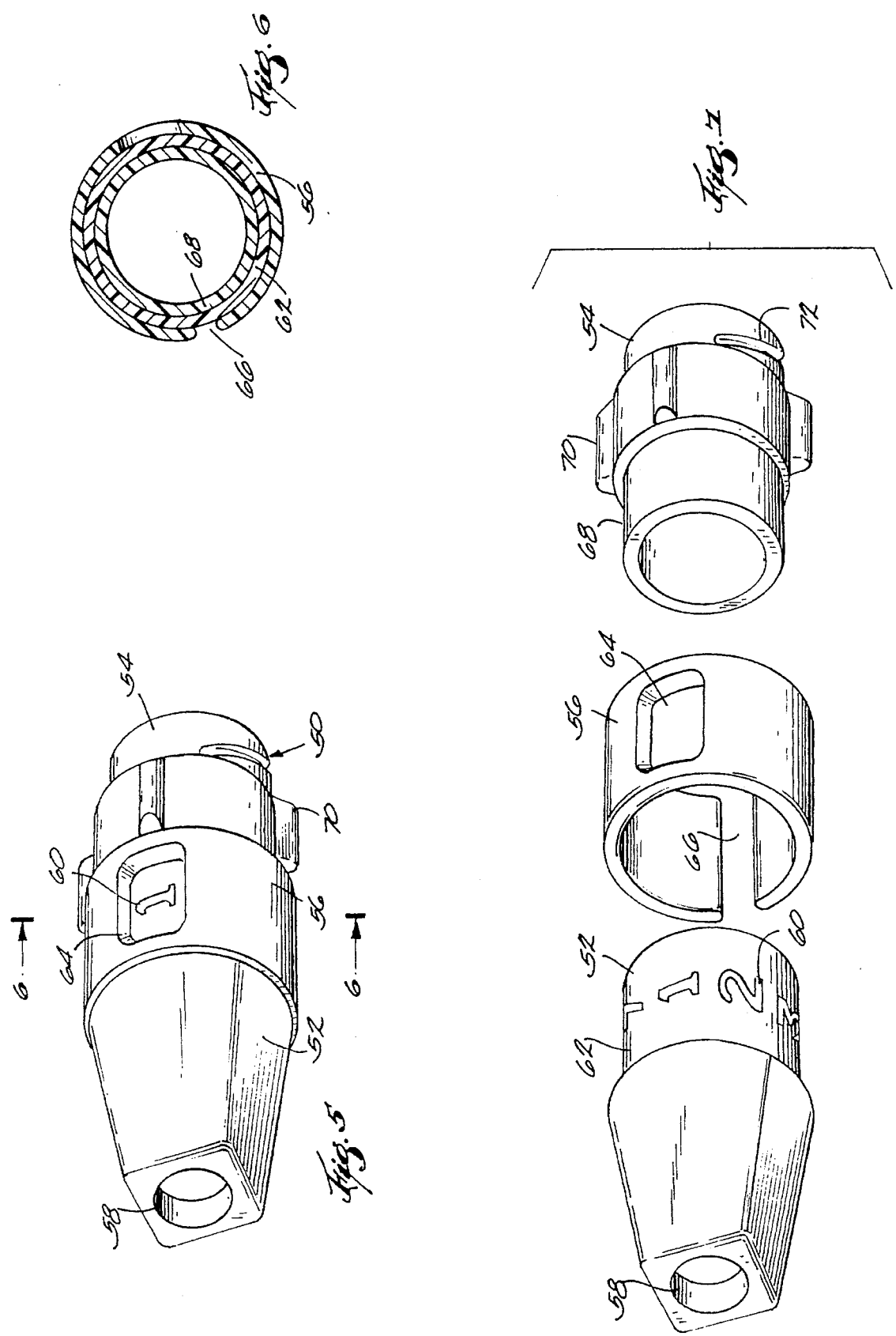

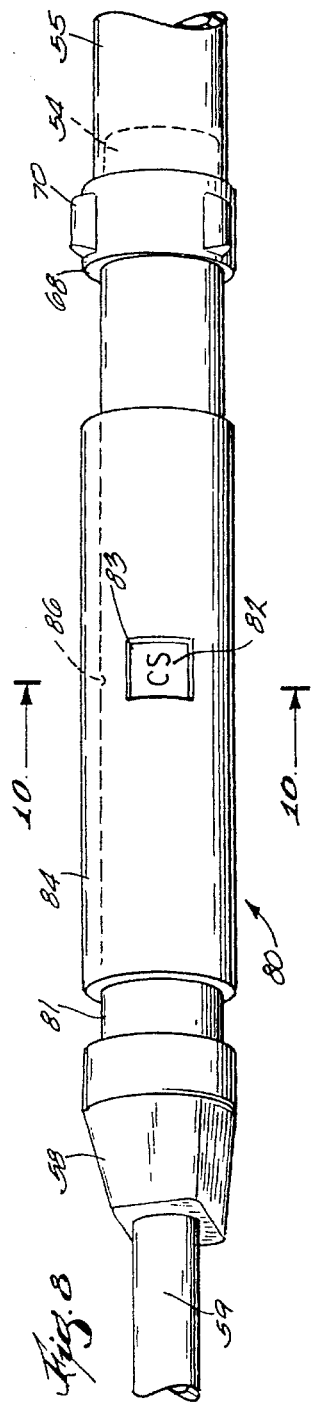
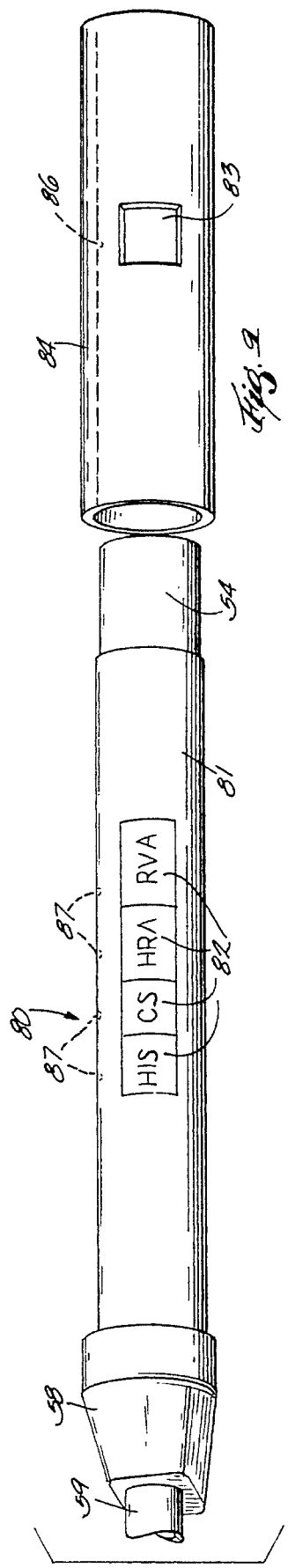
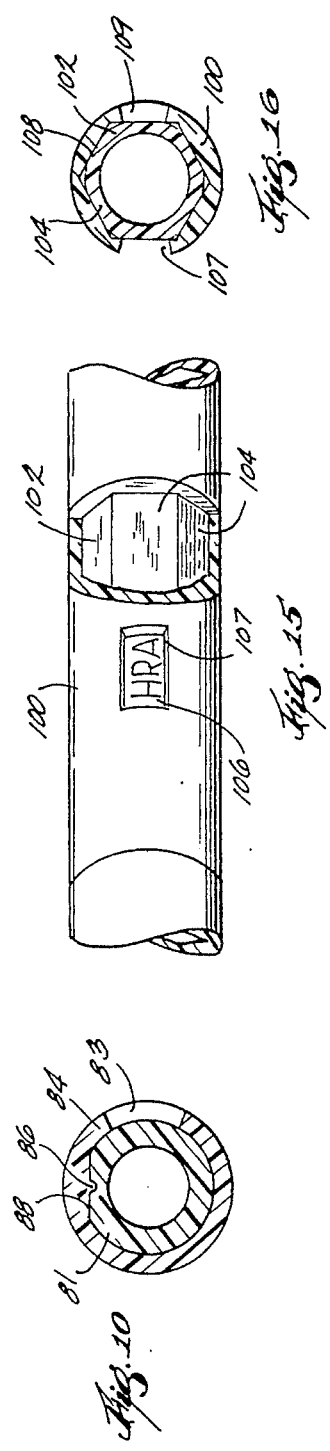

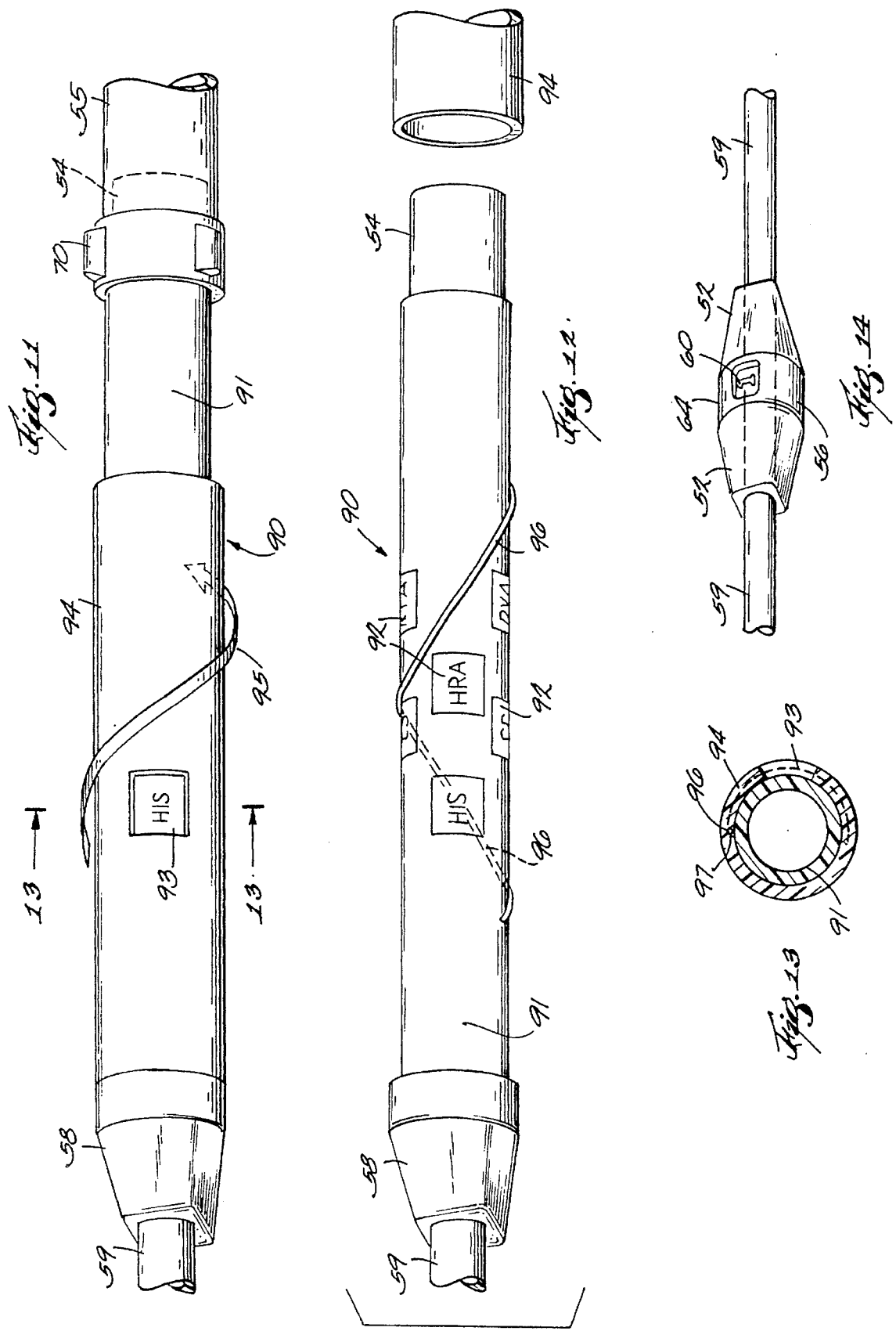

IDENTIFICATION RING FOR CATHETER

FIELD OF THE INVENTION

This invention relates to catheters of the type used for introduction into a body cavity or organ for diagnostic or therapeutic purposes. More specifically, the invention relates to a system for identifying individual catheters of this general type.

BACKGROUND OF THE INVENTION

Diagnostic and therapeutic catheters are used commonly by physicians for diagnosis of conditions within bodily organs or cavities. An important application relates to catheters used for diagnostic or therapeutic purposes within the heart. Various in vivo procedures require the simultaneous use of more than one catheter. For example, several different catheters might be used, each placed within different sites within the heart. Such catheters may be provided with steering mechanisms so that the placement can be accurately controlled from outside the body. Other catheters are non-steerable but are, nonetheless, accurately placed within the body by a physician.

In the past, various catheters have been provided utilizing a color coding system as a means of distinguishing one catheter from another. In such cases, the distinction between catheters is typically linked to the characteristics of the catheter rather than the placement of the catheter within the body. In such systems, however, problems as to maintaining the identity of each of two identical catheters presents difficulty to the physician. A need has, thus, existed for a system for more accurately identifying individual catheters, in these and other similar situations.

SUMMARY OF THE INVENTION

It is a principle object of the invention to provide an improved marking system for distinguishing catheters which makes it easier for a physician to quickly identify a specific catheter from a group of identical catheters which are concurrently used. In accordance with an important aspect of the invention, a movable component such as a ring containing at least one optically transparent area such as a window or an opening and preferably a pair of such areas, is rotatably or slidably mounted on a surface of the catheter, preferably on either the catheter handle, connector cable or the catheter body. Such areas will be referred to hereinafter as "window" whether they are openings, slots, or transparent, but closed, optically transparent areas. In accordance with a related aspect of the invention, a window is selectively alignable with a plurality of marking indicia indicating placement sites located within a bodily organ.

In the case of catheters used for placement within sites within the human heart, the commonly used placement sites within the heart are abbreviated so that they can selectively be brought into alignment with a window for providing an identification label. In accordance with a still further related aspect, abbreviations are preprinted for selective alignment with a window which abbreviations stand for various routinely examined locations within the heart chamber.

In accordance with a yet further aspect of the invention, the device of the present invention has particular applicability to diagnostic catheters which have connector housings and which may be either steerable or non-steerable. In accordance with a preferred embodiment of the invention, the connector housing is modified to be provided with an adjustable ring with either one window or two windows 180° apart from each other. The ring itself may be provided in different colors to signify the specific catheter curve type. As the ring is rotated it makes visible a set of letters, numbers, or icons to identify the specific catheter. Locking projections are provided on the ring or on the part underlying the ring to provide a means for selectively locking the catheter in alignment with the desired marking. In accordance with further embodiments of the invention, the movable component can be fitted to slide axially or to simultaneously slide and rotate to selectively place one or more openings in alignment with appropriate identifying markings.

Briefly, the invention provides a catheter assembly which has a distal end adapted for insertion into a living body and a proximal end adapted to remain external to said body includes said assembly including a surface, which may be cylindrical, on which are inscribed a plurality of markings. Each of the markings indicates one of a plurality of locations within the living body at which the distal end may be placed during insertion, the markings being positioned at spaced intervals on the surface, for example, around the circumference of a cylindrical surface. A sleeve or similar component with a window for selectively exposing selected markings is movably mounted on the surface. In a preferred embodiment, the sleeve or similar movable component is provided with at least one window adapted to be rotated or otherwise moved into alignment with a selected one of the markings.

Further objects and advantages of the invention will be apparent from the following detailed description, the claims, and the accompanying drawings.

BRIEF SUMMARY OF THE DRAWINGS

FIG. 1 is a perspective view with hidden parts shown by phantom lines and showing the use of the invention on a catheter handle;

FIG. 2 is a perspective view of assembly of FIG. 1 with the parts shown in a disassembled relationship for clarity;

FIG. 3 is a fragmentary sectional view taken along line 3—3 of FIG. 1;

FIG. 4 is a sectional view taken along line 4—4 of FIG. 1;

FIG. 5 is a perspective view of a catheter cable attachment assembly showing a different embodiment of the invention;

FIG. 6 is a sectional view taken along line 6—6 of FIG. 5;

FIG. 7 is a fragmentary perspective view of the assembly of FIG. 5 with parts shown in a disassembled relationship for clarity;

FIG. 8 is a fragmentary perspective view showing yet another embodiment of the invention;

FIG. 9 is a perspective view of the assembly of FIG. 8 with parts shown disassembled for clarity;

FIG. 10 is a sectional view taken along line 10—10 of FIG. 8;

FIG. 11 is a fragmentary perspective view showing yet another embodiment of the invention;

FIG. 12 is a perspective view of the assembly of FIG. 11 in a disassembled relationship for clarity;

FIG. 13 is a sectional view taken along line 13—13 of FIG. 11;

FIG. 14 is a fragmentary perspective view showing yet another embodiment of the invention;

FIG. 15 is a fragmentary perspective view with parts cut away to show interior details of yet another embodiment of the invention; and FIG. 16 is a sectional view taken through the windowed portion of the device shown in FIG. 15.

DETAILED DESCRIPTION OF PREFERRED EMBODIMENTS

Referring more specifically to the drawings, there is shown in FIGS. 1–4 a catheter handle distal end assembly 10. Assembly 10 includes a tapered sleeve 12 having a central opening 14 adapted to receive a catheter body (not shown). A cylindrical surface of handle 12 is provided with printed inscriptions 16 which may be in the form of lettering, numbering or icons, as desired. A sleeve 18 is rotatably positioned concentrically around cylindrical portion 16. Cylindrical sleeve 18 is provided with one or preferably two windows 20 and 22. If two windows 20 and 22 are utilized, it is preferred that they be located 180° on opposite sides of sleeve 18. The inscriptions on cylindrical portion 16 of handle 12 are then provided with identical inscriptions 180° apart from each other so that the same message is viewable through window 22 as through window 20. Optionally, a single window 20 can be provided and window 22 omitted. This will provide a single point of indication of the location of the particular catheter to the physician. It is preferred, however, to have two windows spaced 180° from each other in order to facilitate reading of the identification symbol 16. An end piece 24 is provided and adapted to the connected, by means of an adhesive to the proximal end of component 12. Sleeve 24 is also adapted to be connected as required to further proximal handle components of a catheter. Sleeve component 24 may be preferably provided with indentations 26 adapted to receive a projection 28 or 30 on the inside of sleeve 18. This enables locking of sleeve 18 in any one of a plurality of rotational positions to align windows 20 and 22 with a desired pair of inscriptions 16. The mating of tabs 28 and 30 with indentations 26 provides a détente for a releasable locking of sleeve 18 in a desired rotational orientation so that the identification is not inadvertently changed.

The specific inscriptions on the cylindrical surface 16 will vary in accordance with the intended placement of a particular catheter. In the case of cardiac catheters, for example, the identification inscriptions may be HIS (for HIS bundle), CS (for coronary sinus), HRA (for high right atrium) and RVA (for right ventricular apex). The invention, as noted, is not limited to a particular inscription but will vary in accordance with intended location of a specific catheter within a living body.

In accordance with a further embodiment of the invention shown in FIGS. 5–7 the cylindrical surface bearing the inscriptions is on a proximal part of the catheter handle which provides a connection of an electrical cable to the catheter. In the modified embodiment, a catheter handle proximal end assembly 50 is provided with a tapered sleeve 52 which is connected to an end piece or sleeve 54. Sleeve 56 is rotatably mounted on the cylindrical end 62 of tapered sleeve 52. Cylindrical portion 62 contains indicia 60. Sleeve 52 contains an opening 58 at its proximal end for placement therein of a cable assembly for connecting the catheter to an external power supply. As best seen in FIG. 7, sleeve 56 contains an opening or window 64 and a slotted or open portion 66. Window 64 and open slot 66 both provide access to viewing of indicia 60. Window 66, which is in the form of an open slot 66 also enables sleeve 56, which is slightly undersized, to flex and thus to fit tightly around cylindrical portion 62. This provides the ability to form the components 52 and 56 such that a tight frictionally engaging fit is provided which resists free rotation of the components but enables movement or rotation thereof when needed to change the indicia 60 that is visible through the window 64 and/or slot 66.

Sleeve 68 can be provided with ribbed projections 70 to facilitate finger rotation thereof for the purpose of securing the same to the proximal end of a catheter handle by means of threads 72.

Referring specifically to FIGS. 8–10, there is seen a different embodiment of the invention wherein an assembly 80 is adapted to display a selected one from a plurality of indicia relating to the use of a catheter by means of a movable member that slides rather than rotates. To this end, a surface 81 is provided upon which a series of indicia 82 are applied. Indicia 82 are selectively visible through a window 83 provided in a sleeve 84 that is slidably positioned around surface 81. In the illustrated embodiment, the assembly is shown in relation to a connector cable 59. However, the assembly can be attached to an end of a distal end of a catheter handle that is attached to the catheter body, itself.

In connection with the embodiment of FIGS. 8–10, the sleeve 84 is provided with an internal projection 86 which is selectively receivable in any one of a series of indentations 87 provided in surface 81. Indentations 87 are appropriately placed relative to projection 86 so that the projection and indentation serve as a détente to maintain the alignment of window 83 with a selected one of the indicia. The provision of such détente minimizes the possibility of inadvertent moving of sleeve 84 relative to surface 81. As seen in FIG. 10, surface 81 may be provided with a flattened axially aligned portion 88 which slidably receives a mating surface on the interior of sleeve 84, thus preventing sleeve 84 from rotating relative to surface 81. Rather than using an annular sleeve 84, it will be apparent to those skilled in the art that a member that engages less than the entire circumference of surface 81 could be substituted.

Referring to the embodiments of FIGS. 11–13, there is seen a modified assembly 90 which includes a surface 91 upon which a series of indicia 92 are placed in a generally spiral orientation relative to surface 91. A window 93 is provided in a sleeve 94 that is fitted around surface 91 for a generally spiral axial and rotational movement indicated by arrow 95.

The generally spiral motion is produced by the presence of a thread-like projection 96 spirally oriented around surface 91 as seen in FIG. 12. The interior of sleeve 94 is provided with a diagonal groove 97 that causes a simultaneous axial and rotational generally spiral movement of sleeve 94 relative to surface 91. A series of detentes can be provided between sleeve 94 and surface 91 as generally shown with respect to the embodiment of FIGS. 8–10.

Referring to FIG. 14, there is seen a modified embodiment of the invention suitable for placement of an identification device according to the invention anywhere along the length of a connector cable 59. In this embodiment, a pair of tapered sleeves are adhered to the exterior of cable 59 as shown to act as retaining devices for a rotatable ring 56 which is provided with at least one window 64 to selectively make visible one of a plurality of indicia 60. It will be apparent that this embodiment can be further modified to place indicia 60 directly on the exterior surface of cable 59. In such event, the interior diameter of sleeve 56 would be reduced so as to fit closely around the exterior of cable 59.

Also, in this case, it is preferable to place detente projections and indentations along the lateral interface between sleeves 56 and 52.

Referring to FIGS. 15 and 16, a further embodiment is shown wherein sleeve 100 and surface 102 are provided with facets 104. As shown in FIG. 16, a hexagonal shape is provided, but it is equally possible to use other numbers of facets, for example, 8. The sleeve 100 is provided with windows 107 and 109 to selectively make one of a plurality of indicia 106 visible. It is desirable that the corners of facets 104 be somewhat rounded so that the sleeve 100 can be rotated over the interior member 102 and to provide a detente or resistance to rotation so that the setting of the devices is not inadvertently or accidentally changed during the procedure involving the catheter. In such event, the interior facets 108 of sleeve 100 can be provided with sharper interior corners than the exterior of component 102.

In connection with each of the foregoing embodiments, similar numbers are used to indicate similar parts which are, thus, not redescribed in connection with each of the embodiments.

While the embodiments of the invention hereinbefore described are effectively adapted to fulfill the objects of the invention, it is to be understood that the invention is not intended to be limited to the specific preferred embodiments set forth above. Rather, it is to be taken as including all reasonable equivalents within the scope of the following claims.

What is claimed is:

1. A catheter assembly having a distal end adapted for insertion into a living body and a proximal end adapted to remain external to said body, said assembly including a surface for placement of marking indicia, a plurality of marking indicia each indicating one of a plurality of locations within the living body at which said distal end may be placed during insertion, said markings being positioned at spaced intervals on said surface, and a member located on said assembly for movement on said surface, said member being provided with at least one window adapted to be moved into alignment with a selected one of said markings so that said selected marking is visible through said window.

2. An assembly according to claim 1 wherein said member is in the form of a split annular ring.

3. An assembly according to claim 2 wherein said split annular ring has a window therein located 180° around the circumference thereof from said split.

4. An assembly according to claim 1 wherein said surface is cylindrical and is located on a component which forms a proximal end assembly attached to the proximal end of a handle attached to said catheter, said component having a passage therethrough for connection of said catheter to external therapeutic, monitoring or diagnostic equipment.

5. An assembly according to claim 1 wherein either said member or said surface is provided with a projection engageable with a plurality of mating indentations in the other of said member or said surface to provide a détente to selectively secure said window in alignment with a selected one of said indicia.

6. An assembly according to claim 1 wherein said member is axially slidable along said surface in a generally spiral path.

7. An assembly according to claim 1 wherein said member is both axially and rotationally movable along said surface.

8. A catheter assembly having a distal end adapted for insertion into a living body and a proximal end adapted to remain external to said body, said assembly including a cylindrical surface, a plurality of markings each indicating one of a plurality of locations within the living body at which said distal end may be placed during insertion, said markings being positioned at spaced intervals around the circumference of said cylindrical surface, and a sleeve located rotatably mounted around said cylindrical surface, said sleeve being provided with at least one window adapted to be rotated into alignment with a selected one of said markings.

9. A catheter assembly according to claim 1 wherein said surface is on a connector cable attached to said catheter.

10. A catheter assembly according to claim 1 wherein said surface is on a sleeve positioned around a connector cable attached to said catheter.

11. A connector cable attachable to a catheter to form an assembly having a distal end adapted for insertion into a living body and a proximal end adapted to remain external to said body, said cable including a surface for placement of marking indicia, a plurality of marking indicia each indicating one of a plurality of locations within the living body at which said distal end may be placed during insertion, said markings being positioned at spaced intervals on said surface, and a member located on said cable for movement on said surface, said member being provided with at least one window adapted to be moved into alignment with a selected one of said markings so that said selected marking is visible through said window.

12. A cable according to claim 11 wherein said surface comprises the outer surface thereof.

13. A cable according to claim 11 wherein said surface is on a sleeve positioned around a said cable.

\* \* \* \* \*